(12) United States Patent
Chan et al.

(10) Patent No.: US 9,939,623 B2
(45) Date of Patent: Apr. 10, 2018

(54) MICROSCOPE SYSTEM WITH TRANSILLUMINATION-BASED AUTOFOCUSING FOR PHOTOLUMINESCENCE IMAGING

(71) Applicant: MOLECULAR DEVICES, LLC, Sunnyvale, CA (US)

(72) Inventors: Matthew Chan, Palo Alto, CA (US); Nia W. Fong, Menlo Park, CA (US); Robert Malcolm Watson, Jr., Castro Valley, CA (US)

(73) Assignee: Molecular Devices, LLC, San Jose, CA (US)

( * ) Notice: Subject to any disclaimer, the term of this patent is extended or adjusted under 35 U.S.C. 154(b) by 161 days.

(21) Appl. No.: 14/886,998

(22) Filed: Oct. 19, 2015

(65) Prior Publication Data
US 2017/0108686 A1    Apr. 20, 2017

(51) Int. Cl.
| | |
|---|---|
| *G02B 15/22* | (2006.01) |
| *G02B 21/24* | (2006.01) |
| *G02B 21/16* | (2006.01) |
| *G02B 21/08* | (2006.01) |
| *G01N 21/64* | (2006.01) |
| *G02B 7/38* | (2006.01) |

(Continued)

(52) U.S. Cl.
CPC ....... *G02B 21/244* (2013.01); *G01N 21/6452* (2013.01); *G01N 21/6458* (2013.01); *G02B 7/38* (2013.01); *G02B 21/086* (2013.01); *G02B 21/16* (2013.01); *G02B 21/26* (2013.01); *G02B 21/367* (2013.01)

(58) Field of Classification Search
CPC .... G02B 21/244; G02B 21/086; G02B 21/16; G02B 21/26; G02B 21/367; G02B 7/38; G01N 21/6452; G01N 21/6458
See application file for complete search history.

(56) References Cited

U.S. PATENT DOCUMENTS

| | | | | |
|---|---|---|---|---|
| 5,790,710 A | * | 8/1998 | Price ................. | G01N 15/147 250/201.3 |
| 2003/0228038 A1 | * | 12/2003 | Douglass ............ | G01N 1/312 382/128 |

(Continued)

OTHER PUBLICATIONS

Ali, Rehan, et al., Phase-Based Segmentation of Cells From Brightfield Microscopy, IEEE, 1-4244-0672-2/07, 2007, pp. 57-60.

(Continued)

*Primary Examiner* — Christopher Findley

(57) ABSTRACT

Microscope system for, and methods of, imaging a sample including biological cells. In an exemplary method, light transmitted through the sample may be detected for a first set of focal positions to collect a first stack of images. Values of a focus metric may be calculated for the first stack of images. A candidate focal position may be determined based on the values. Photoluminescence may be detected from the sample for a second set of focal positions to collect a second stack of images. The second set of focal positions may define a smaller range than the first set of focal positions. At least one focal position of the second set of focal positions may be based on the candidate focal position. In other words, the candidate focal position may serve as a guide for finding a suitable photoluminescence focal position.

20 Claims, 6 Drawing Sheets

(51) Int. Cl.
  *G02B 21/36*   (2006.01)
  *G02B 21/26*   (2006.01)

(56) References Cited

U.S. PATENT DOCUMENTS

| | | | |
|---|---|---|---|
| 2005/0089208 A1* | 4/2005 | Dong | G02B 21/241 |
| | | | 382/133 |
| 2012/0007977 A1* | 1/2012 | Yamamoto | G02B 27/0075 |
| | | | 348/79 |
| 2015/0054921 A1* | 2/2015 | Dixon | G02B 21/26 |
| | | | 348/46 |
| 2015/0185460 A1* | 7/2015 | Nakasho | G02B 21/16 |
| | | | 250/459.1 |

OTHER PUBLICATIONS

Marrison, Joanne, et al., Ptychography—a label free, high-contrast imaging technique for live cells using quantitative phase information, Scientific Reports 3: 2369 DOI: 10.1038/srep02369, Aug. 6, 2013, pp. 1-7.
Mualla, Firas, et al, Automatic Cell Detection in Bright-Field Microscope Images Using SIFT, Random Forests, and Hierarchical Clustering, IEEE, 2013, pp. 1-14.

* cited by examiner

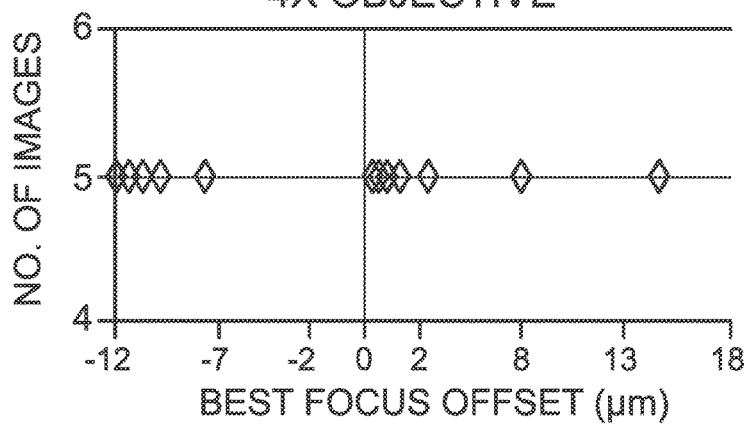
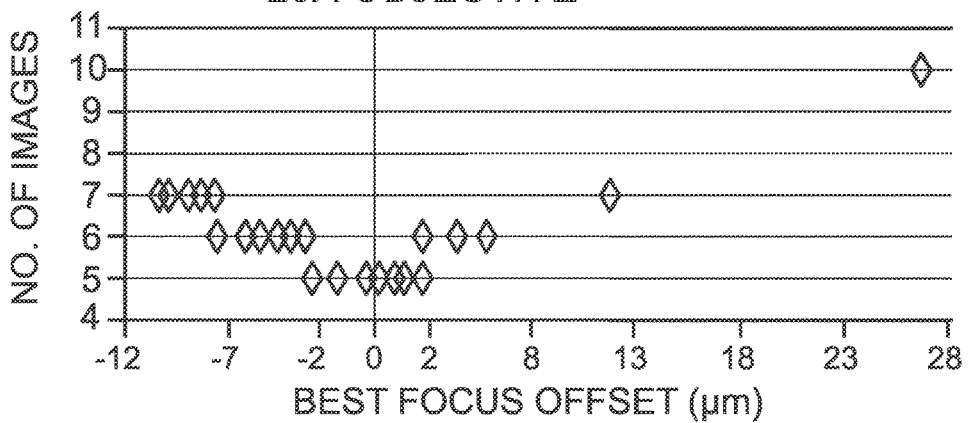

MICROSCOPE SYSTEM WITH TRANSILLUMINATION-BASED AUTOFOCUSING FOR PHOTOLUMINESCENCE IMAGING

INTRODUCTION

Cells are imaged in many research and clinical applications. For example, the cells may be exposed to effectors in a high throughput screen, serve as a model system for studying a physiological process, or constitute a clinical sample for disease diagnosis, among others. A cellular feature of particular interest can be visualized by staining with a fluorescent dye that binds selectively to a localized target(s) present in or on the cells. The stained cells can be imaged by illumination with excitation light and then detection of the resulting fluorescence emission.

Fluorescence imaging of cells in an automated environment presents particular challenges. Exposure of the cells to excitation light can alter the fluorescent dye to a nonfluorescent form permanently over time by photobleaching. Accordingly, the fluorescence signal detected from the cells is diminished through photobleaching as the cells are imaged at different focal positions in an attempt to find the best focus. A related challenge is to determine a suitable exposure time for image collection; the level of staining affects the exposure time and can vary significantly with different samples, reagents, and/or staining procedures. It can be difficult to find a suitable exposure time for all of the fluorescence images to be collected in a field of view, when there is no estimate available for the best focal position. Fluorescence images inadvertently collected far from the best focal position often provide little information about an appropriate exposure time for subsequent images collected closer to the best focal position. Better autofocusing approaches are needed for photoluminescence imaging of cells.

SUMMARY

The present disclosure provides a microscope system for, and methods of, imaging a sample including biological cells. In an exemplary method, light transmitted through the sample may be detected for a first set of focal positions to collect a first stack of images. Values of a focus metric may be calculated for the first stack of images. A candidate focal position may be determined based on the values. Photoluminescence may be detected from the sample for a second set of focal positions to collect a second stack of images. The second set of focal positions may define a smaller range than the first set of focal positions. At least one focal position of the second set of focal positions may be based on the candidate focal position. In other words, the candidate focal position may serve as a guide for finding a suitable photoluminescence focal position.

BRIEF DESCRIPTION OF THE DRAWINGS

FIG. 8 is a graph plotting an offset of the best focal position for photoluminescence as a function of the number of photoluminescence images collected, with data in the graph obtained with an embodiment of the microscope system of FIGS. 1A and 1B equipped with a 4× objective.

FIG. 9 is a graph plotting an offset of the best focal position for photoluminescence as a function of the number of photoluminescence images collected, with data in the graph obtained with an embodiment of the microscope system of FIGS. 1A and 1B equipped with a 20× objective.

DETAILED DESCRIPTION

Figure 1A:
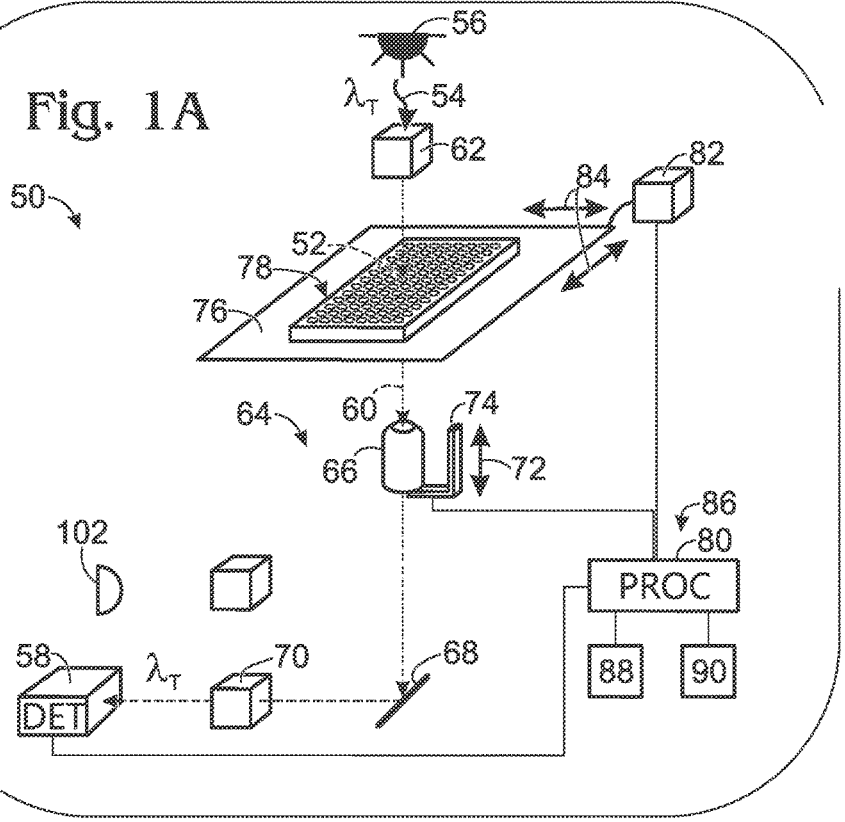
FIG. 1A is a schematic view of an exemplary microscope system for photoluminescence imaging, where the system is equipped with a transillumination-based image autofocusing mechanism, with the system shown during transillumination of a sample and detection of an image created by transmitted light, in accordance with aspects of the present disclosure.

The present disclosure provides a microscope system for, and methods of, imaging a sample including biological cells. In an exemplary method, light transmitted through the sample may be detected for a first set of focal positions to collect a first stack of images. Values of a focus metric may be calculated for the first stack of images. A candidate focal position may be determined based on the values. Photoluminescence may be detected from the sample for a second set of focal positions to collect a second stack of images. The second set of focal positions may define a smaller range than the first set of focal positions. At least one focal position of the second set of focal positions may be based on the candidate focal position. In other words, the candidate focal position may serve as a guide for finding a suitable photoluminescence focal position.

Another exemplary method of imaging a sample including biological cells is provided. Light transmitted through the sample may be detected for a set of focal positions to collect a stack of images. Values of a focus metric may be calculated for the stack of images. A candidate focal position may be determined based on the values. A photoluminescence focal position may be obtained based on the candidate focal position. A photoluminescence image of the sample may be detected with the photoluminescence focal position. In some embodiments, the photoluminescence focal position is the same as the candidate focal position or is related to the candidate focal position by a predefined offset.

The microscope system of the present disclosure may have various advantages over other microscope systems for automated photoluminescence (e.g., fluorescence) imaging. First, the system may be able to image each field of view faster, due to a lower number of photoluminescence images collected for the field of view. The system also may be faster because transillumination images can be collected faster than photoluminescence images due to a shorter exposure time. Second, use of transillumination for determining a candidate focal position allows a greater search range along the optical axis, and thus reduces the chance that the search range will not contain the best focus. Third, transillumination may produce much less photobleaching than epi-illumination (for photoluminescence excitation), so an approximate focus for photoluminescence can be determined before any substantial photobleaching occurs. Fourth, the candidate focal position determined with transillumination is close to the best focus for photoluminescence, which allows a suitable, predetermined exposure time for each other image of a stack of photoluminescence images to be determined at the initial focal position where the initial image is collected for the stack. The total intensity of photoluminescence detected for each image of the stack does not vary significantly because each image is relatively close to the best focus. Fifth, two or more images of the stack of bright-field (transillumination) images and/or two or more images of the stack of photoluminescence images may be at least partially combined (also called blended) with one another by image processing to produce a digital phase image and/or a best Z position projection, respectively.

Further aspects of the present disclosure are described in the following sections: (I) overview of microscope imaging systems, (II) methods of autofocus-based photoluminescence imaging, and (III) examples.

I. Overview of Microscope Imaging Systems

This section provides an overview of an exemplary microscope system 50 for photoluminescence imaging, where the system is equipped with a transillumination-based image autofocusing mechanism; see FIGS. 1A, 1B, 2, and 3.

FIG. 1A shows microscope system 50 during transillumination of a sample 52 with transmitted light 54 ($\lambda_T$) produced by a transillumination light source 56 (also called a bright-field source). Light 54 is transmitted through sample 52 and is detected by an image detector 58. The image detector collects images of sample 52 by detecting transmitted light. The images produced by transillumination interchangeably are called transillumination images or bright-field images. Light source 56 may be any suitable source, such as a light-emitting diode(s), a mercury arc lamp, a laser, or the like.

Light, as used herein, may include optical radiation of any suitable wavelength. Accordingly, light may be any combination of visible radiation, ultraviolet radiation, and/or infrared radiation.

Image detector 58 may be any device for collecting images of a sample. Exemplary image detectors include charge-coupled device (CCD) sensors, active pixel sensors (e.g., complementary metal-oxide-semiconductor (CMOS) sensors, N-type metal-oxide-semiconductor (NMOS) sensors, etc.), or the like.

The sample may be disposed in a plane, generally a horizontal plane (also called an xy plane), and light source 56 and image detector 58 may (or may not) be located on opposite sides of the plane from one another. For example, in the depicted embodiment, light source 56 is disposed above the xy plane and the sample, and image detector 58 is disposed below the xy plane and the sample. In an inverted configuration, the light source may be disposed below the sample, and the image detector may be disposed above the sample.

An optical axis 60 of system 50 extends from light source 56 to detector 58. The optical axis may extend vertically through sample 52 along a z-axis. For the purposes of this disclosure, the optical axis and the z-axis will be used interchangeably, even though the optical axis may not be vertical along all (or any) of its length.

Transmitted light 54 may travel to sample 52 from bright-field source 56 via illumination optics 62, and from the sample to image detector 58 via collection optics 64. Each of illumination optics 62 and collection optics 64 may have one or more optical elements. An optical element may be any device or structure that collects, directs, and/or focuses light and/or partially blocks light. An optical element may function by any suitable mechanism, such as reflecting, refracting, diffracting, and/or filtering light, among others. Exemplary optical elements include lenses, mirrors, gratings, prisms, filters, apertures, beam splitters, transmissive fibers (fiber optics), or the like.

Illumination optics 62 may include at least one optical element, such as a lens or an aperture, that substantially collimates light from bright-field light source 56. The collimated light may (or may not) be slightly diverging or slightly converging (e.g., to form a cone angle with respect to the optical axis of less than 5, 3, 2, or 1 degree(s) and/or greater than 0.5, 1, or 2 degrees, among others). Divergence or convergence of the light may improve the quality of a focus metric calculated from bright-field images collected with transmitted light from light source 56.

In the depicted embodiment, collection optics 64 includes an objective 66, a fold mirror 68, and a tube lens 70. Objective 66 may be composed of one or more optical elements, which may be fixed in position relative to one another. The positional relationship of the sample 52 and objective 66 relative to one another defines the focal position (also called the focus) of the system. More particularly, the distance of the objective from the sample along the z-axis (and/or optical axis) defines the focal position and determines whether or not the sample is in focus our out of focus in the image plane. The focal position may be adjusted by moving sample 52, objective 66, or both. In exemplary embodiments, the focal position is adjusted by moving the objective, indicated with an arrow at 72. The objective may be moved along the z-axis by a drive mechanism 74 operatively connected to the objective, while the sample remains stationary. In other embodiments, the drive mechanism may be operatively connected to a stage 76 supporting a sample holder 78 that contains sample 52, such that the focal position is adjusted while the objective remains stationary. In any event, the drive mechanism may be in communication with and controlled by a digital processor 80, to permit automated adjustment of the focal position.

Processor 80 may be in communication with and/or may control operation of any suitable combination of devices of system 50, and may be equipped with any suitable algorithms for automating operation of the system. The processor may receive and process image data from image detector 58. Processor 80 also may control a stage drive mechanism 82 that drives movement of stage 76 parallel to the xy plane, indicated by arrows at 84. Control of stage drive mechanism 82 may allow the system to automate imaging of multiple samples, multiple locations within the same sample, and/or multiple fiducials, among others. The processor also may control switching between transillumination and epi-illumination, and thus between collection of bright-field images and photoluminescence images.

Processor 80 may be provided by a computing system or computer 86. The computer may include a display 88, a user interface 90, memory to store algorithms and data, and the like.

Figure 1B:
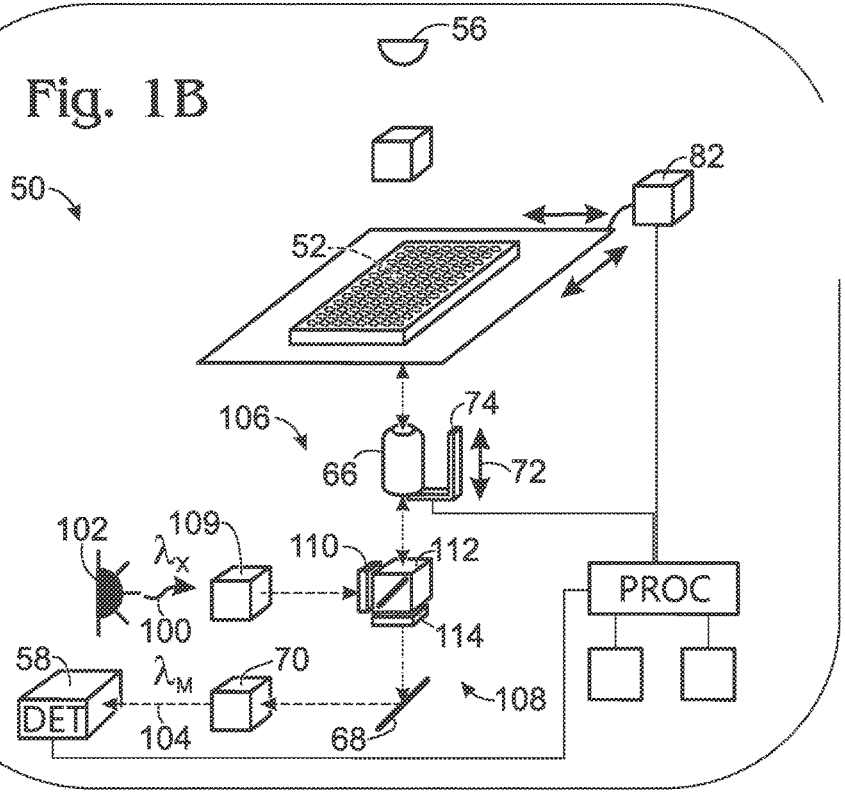
FIG. 1B is another schematic view of the microscope system of FIG. 1A, with the system shown during epi-illumination of the same sample and field of view as in FIG. 1A and detection of a photoluminescence image created by light emitted via photoluminescence.

FIG. 1B shows microscope system 50 during epi-illumination of the same field of view of sample 52 with excitation light 100 ($\lambda_X$) produced by an excitation light source 102. Excitation light 100 excites a photoluminophore (e.g., a fluorescent dye) in the sample, which causes the photoluminophore to photoluminesce, namely, to generate emitted light 104 ($\lambda_M$) that is detected by image detector 58. The image detector collects photoluminescence images of sample 52 by detection of emitted light 104. Photoluminescence includes any photo-induced emission of light, such as fluorescence, phosphorescence, and the like.

Excitation light 100 may travel to sample 52 from excitation source 102 via illumination optics 106, and from the sample to image detector 58 via collection optics 108. However, in contrast to the transillumination configuration of FIG. 1A, one or more optical elements of optics 106 and 108 may be shared with one another, because excitation light 100 and emitted light 104 travel to and from sample 52 on the same optical path below or above the sample. Illumination optics 106 may include any combination of a source-associated optical element 109 (e.g., an aperture or refractive element, among others), an excitation filter 110, a beam splitter 112, and objective 66. Collection optics 108 may include any combination of objective 66, beam splitter 112, an emission filter 114, fold mirror 68, and tube lens 70.

Other components of system 50 described above for transillumination may or may not be in use. For example, bright-field source 56 may be turned off such that no transillumination light is detected. Objective drive mechanism 74, stage drive mechanism 82, and computer 86 remain operational.

Sample 52 may be any suitable material, substance, isolate, extract, particles, or the like. The sample may include biological cells to be imaged. The biological cells may eukaryotic or prokaryotic, and may be alive or dead (e.g., fixed). Exemplary biological cells include established cells (cell lines), primary cells, cells from a tissue sample, cells from a clinical sample (e.g., a blood sample, a fluid aspirate, a tissue section, etc.), bacterial cells, or the like. The cells may produce a photoluminescent substance (e.g., green fluorescent protein (GFP)) or may be stained with a photoluminophore (e.g., after the cells have been fixed).

Sample holder 78 may be any device for holding at least one sample or any array of spatially isolated samples. The sample holder may provide a substrate having at least one horizontal, upward-facing surface region (a location) on which biological cells of a sample may rest and/or be attached. The sample holder may have only one surface region for cell attachment, or multiple surface regions or compartments separated from one another. Each surface region may include a coating to encourage cell attachment. The coating may, for example, be poly-lysine, collagen, or the like. The coating may be located on a body of the sample holder, which may be formed of transparent plastic or glass, among others. Exemplary sample holders include a culture dish, a multi-well plate (e.g., having 4, 6, 8, 12, 24, 32, 48, or 96 wells, among others), and a slide providing a single compartment or a plurality of discrete compartments for holding cells, among others.

Figure 2:
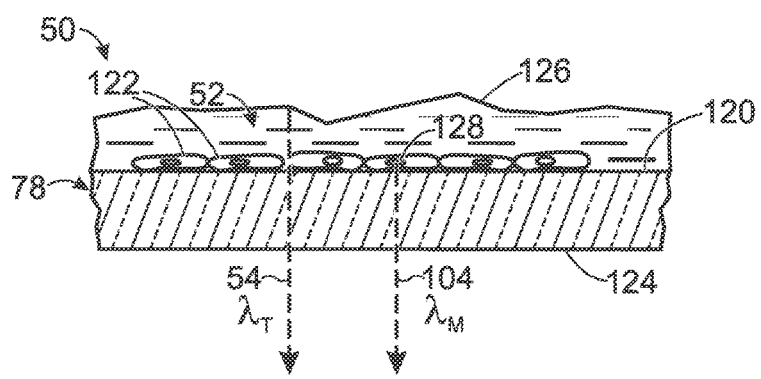
FIG. 2 is a sectional, fragmentary, schematic view of the microscope system of FIGS. 1A and 1B, taken through a well of a sample holder of the system, with the well holding biological cells to be imaged, and with transmitted light and emitted light shown together in the same view to allow comparison, in accordance with aspects of the present disclosure.

FIG. 2 shows a portion of sample holder 78 of system 50. The sample holder is a multi-well plate having a plurality of wells 120 each capable of holding a different sample 52 (see FIG. 1). An exemplary sample 52 present in one of wells 120 is shown here. The sample includes a plurality of biological cells 122 disposed on and optionally attached to a substrate 124 that forms a floor of the well. Cells 122 may remain covered by a liquid medium 126, such as a tissue culture medium, an aqueous buffer, water, or the like, while cells are being imaged. The cells may form a monolayer or may be stacked on top of one another. The cells may or may not be flat, and the organelle or other cellular structure or component that is stained may be anywhere within or on the cell. In many cases, the substrate may not be flat on top (e.g., it may have a wedge or may be bowed).

Transmitted light 54 and emitted light 104 are shown together in FIG. 2 to allow comparison, even though transillumination and epi-illumination are generally performed separately, at different times from one another. Cells 122 may act as phase objects when light 54 is transmitted through the cells. Waves of light 54 are diffracted and phase-shifted by features of the cells. The phase shifts generally are not detectable when the cells are in focus, but can produce constructive and/or destructive interference at the image plane when the cells are slightly out of focus. This interference increases the contrast of the collected image when the image is slightly out of focus, relative to in focus. Accordingly, transillumination allows a best bright-field focus to be determined for the approximate vertical center of the cells.

Emitted light 104 may originate from a photoluminophore located within, on, or about the cells. For example, in the depicted embodiment, light 104 is emitted from a stained nucleus 128 of cells 122. The best bright-field focus may or may not be the same as the best photoluminescence focus, depending on which part of cells 122 is photoluminescent (and the height of that part of the cells), the presence or absence of chromatic aberration associated with a difference in wavelength between transmitted light 54 and emitted light 104, or other system differences between trans- and epi-illumination, among others. In other words, an offset, if any, of the best photoluminescence focus from the best bright-field focus may be determined by the sample, system optics, or a combination thereof, among others. The offset may be no more than about 20, 10, or 5 micrometers, among others.

Figure 3:
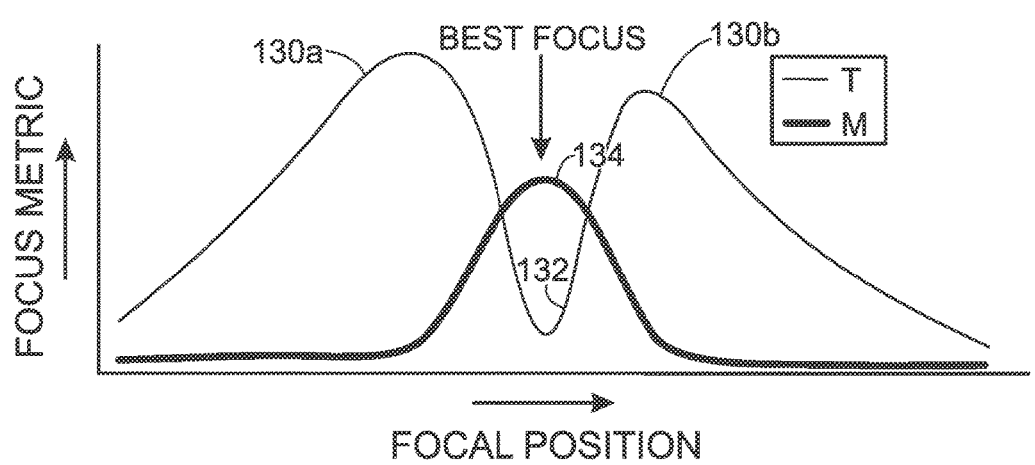
FIG. 3 is a schematic graph plotting a focus metric (i.e., a measure of contrast) as a function of focal position for transmitted light ("T") and emitted light ("M") in the microscope system of FIGS. 1A and 1B.

FIG. 3 shows a graph plotting a focus metric as a function of focal position for transillumination images ("T") and emitted light images ("M") collected with the microscope system of FIGS. 1A and 1B, for the same field of view. The focus metric may be a measure of contrast, which decreases when the transillumination images are collected near the best focal position for transillumination. Accordingly, the values of the focus metric obtained from transillumination images form two contrast peaks 130a, 130b separated by a contrast valley 132. Values of a focus metric (optionally the same focus metric) obtained from photoluminescence images form a single peak 134 at roughly the same focal position as the valley. The apex of the single peak and the nadir of the valley may be located at focal positions that are offset from one another for any of the reasons described above for FIG. 2.

The presence of two contrast peaks 130a, 130b effectively doubles the depth of field for the system. The sampling rate can be cut in half; the presence of two peaks allows aliasing to be used to advantage. Accordingly, a large range of focal positions can be searched for a best focus by collecting only a relatively small number of transillumination images.

II. Methods of Autofocus-Based Photoluminescence Imaging

Figure 4:
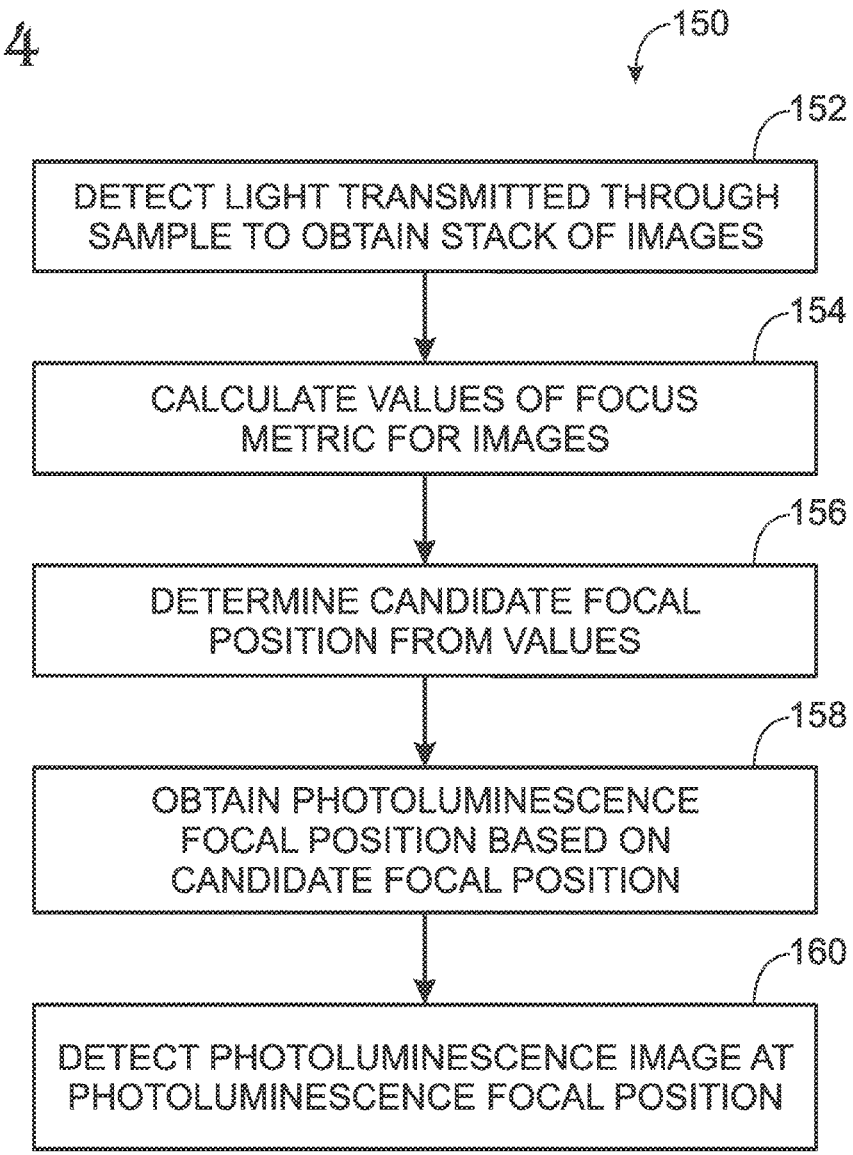
FIG. 4 is a flowchart of an exemplary method of obtaining a photoluminescence image of a sample with the assistance of a transillumination-based autofocusing mechanism.

This section describes exemplary methods of photoluminescence imaging that rely on a candidate focal position obtained from bright-field imaging; see FIG. 4.

FIG. 4 shows a flowchart 150 of an exemplary method of obtaining a photoluminescence image of a sample with the assistance of a transillumination-based autofocusing mechanism. The method steps described in this section may be performed in any suitable combination and order, and may be combined or performed with any other suitable steps, structure, and features of the present disclosure, such as with any suitable devices, configurations, and features of microscope system 50 of Section I.

Light transmitted through a sample may be detected to obtain a stack of bright-field images, indicated at 152. The light may, for example, be visible light of any suitable wavelength(s). The light illuminating the sample may or may not be substantially coherent (such as at least 25%, 50%, or 75% coherent) and may be substantially collimated, but optionally divergent or convergent with respect to perfect collimation. The sample may include one or more biological cells, which may be disposed on and/or attached to a substrate.

The bright-field images may form a z-stack of images collected at a corresponding series of focal positions (e.g., z positions) of a microscope system. The focal positions may span any suitable range, and may have any suitable step (interval) size along the optical axis between adjacent focal positions, to produce any suitable number of images for the range.

The range may be selected based on any suitable criteria. In some embodiments, the lower end of the range may be selected based on a measurement from an optical measuring device that measures the z-position of the bottom side (and/or the top side) of the sample holder on the optical axis. A bottom side z-position as the lower end of the range ensures that the sample is above the lower end of the range, because the sample is elevated from the bottom side of the sample holder by the local thickness of the sample holder on the optical axis. An exemplary optical measuring device is a laser-based measuring device of the microscope system. In other embodiments, a user may communicate the type of sample holder being used to computer 86, and then the computer may select a lower end of the range based on the type of sample holder and its known geometry. Alternatively, the sample holder may include indicia (e.g., a barcode) that are readable by the microscope system automatically to determine the type of sample holder and its known geometry. In some embodiments, a user may select the lower end and/or the upper end of the range, and/or the step size for focal positions within the range, and/or the number of images to be collected over the range. The range may be selected automatically or manually, and may be large enough to encompass at least a portion or at least a majority (e.g., the apices) of both contrast peaks 130a, 130b produced by the focus metric calculated from collected images (e.g., see FIG. 3).

In exemplary embodiments, the z-stack of bright-field images is composed of at least 5, 6, 7, 8, 9, or 10 bright-field images and/or no more than 25, 20, 15, or 12 bright-field images, such as 7-20, 8-15, or 9-12 bright-field images, among others. The bright-field images may be collected starting at one end of the range (or intermediate the ends of the range), with the objective traveling to the other end of the range (or to both ends of the range). The objective may be stopped at each selected focal position over the range before an image is collected, or the objective may travel continuously through the range while images are collected periodically. Pulsed transillumination may be used if the objective travels continuously while images are collected, to improve image quality and/or control the exposure time (also called the exposure duration). The flash rate of transillumination may be selected in conjunction with the travel speed of the objective to establish a desired step size between successive images.

In exemplary embodiments, the size of each focal position step is determined at least in part by the magnification power (and/or numerical aperture (NA)) of the objective, with larger steps being suitable for a low power objective and smaller steps for a medium power objective. A low power objective may, for example, be a 2×, 4×, 10×, or 2×-10× objective, among others, providing the indicated magnification. A medium power objective may, for example, be a 10×, 20×, 40×, or 10×-40× objective, among others. The step size may be decreased as the power of the objective is increased. Exemplary step sizes for a low power objective may be at least or less than 10, 20, 30, 40, 50, or 60 micrometers, among others. Exemplary step sizes for a medium power objective may be at least or less than 1, 2, 3, 4, 5, 7, or 10 micrometers, among others. In some embodiments, a high power objective (40×-100×) may be used.

A value of a focus metric for each of the bright-field images of the z-stack may be calculated, indicated at 154. Any suitable focus metric may be used. Exemplary focus metrics provide a measure of contrast within each image. The measure of contrast may be any suitable contrast indication, prediction, and/or correlation. Suitable algorithms to provide a focus metric are Vollath F4, Vollath F5, Tenengrad, Brenner, normalized variance, sum-modified Laplacian, the energy of the Laplacian, entropy, depth of peaks and valleys, and the like. See Osibote, O. A. et al., J Microsc. 2010 November; 240(2): 155-163 and Santos, A. et al., J Microsc. 1997 December; 188(3): 264-272, which are incorporated herein by reference.

A candidate focal position for photoluminescence imaging may be determined from the values of the focus metric for the z-stack of bright-field images, indicated at 156. The candidate focal position may be an approximation of the best focal position for photoluminescence imaging. (Accordingly, in some embodiments, the candidate focal position may be chosen as a nominally best photoluminescence focal position.) The candidate focal position may be located between contrast peaks 130a, 130b, namely, in contrast valley 132 (see FIG. 3). The candidate focal position may be approximately or exactly at the midpoint between peaks 130a, 130b.

The candidate focal position may be obtained by fitting a curve to the data points for the bright-field images of the z-stack, where each data point is defined by a focal position and a value of the focus metric. The curve may have a single peak, rather than two peaks with transillumination, with an apex of the single peak generally corresponding to the nadir of contrast valley 132 and intermediate contrast peaks 130a, 130b (see FIG. 3). The curve may, for example, be defined by a one-term Gaussian function. With this approach, the candidate focal position is the focal position at which the focus metric is at a maximum along the curve. As described further below in Example 1, the use of a one-term Gaussian function for finding a candidate focal position allows collection of only a sparse stack of bright-field images over a large range of focal positions. The one-term Gaussian may define a candidate focal position that is biased to the left or the right of the actual best focus for transillumination. In other embodiments, a two-term Gaussian function may be utilized.

A photoluminescence focal position may be obtained based on the candidate focal position, indicated at 158. The photoluminescence focal position may be obtained directly from the candidate focal position, optionally before any further imaging is conducted. For example, the candidate focal position may be chosen as the (nominally) best photoluminescence focal position for subsequent photoluminescence imaging of the sample for the same field of view (or other fields of view). As another example, the candidate focal position may be adjusted mathematically by a predetermined offset to produce the (nominally) best photoluminescence focal position for subsequent photoluminescence imaging of the sample for the same field of view (or other fields of view). The predetermined offset accounts for a difference between the transillumination configuration and epi-illumination configurations. The offset may include an instrument offset that accounts for an optical difference (such as chromatic aberration) and/or a mechanical difference, among others. The offset also or alternatively may include a sample offset that accounts for a different average position along the optical axis of sample structures that produce a phase shift of transmitted light, relative to sample structures that are photoluminescent.

Alternatively, a search for the best photoluminescence focal position may be initiated based on the candidate focal position. A set of photoluminescence focal positions for photoluminescence imaging of the sample may be selected based on the candidate focal position. The set of photoluminescence focal positions are utilized to search for a best photoluminescence focal position by refining the candidate focal position. The set of photoluminescence focal positions may define a range of focal positions that encompasses the candidate focal position. The range of focal positions for photoluminescence may be significantly smaller than the range of focal positions used for transillumination, such as no more than about ¾, ⅔, or ½, among others, of the transillumination range, because the candidate focal position generally is a fairly accurate estimate of the best photoluminescence focal position. In some embodiments, the range of photoluminescence focal positions may be no more than about 1.5, 2, 3, or 4 times the depth of field of the objective for photoluminescence. The step size for the set of photoluminescence focal positions also may be significantly smaller than for transillumination, such as no more than about ¾, ⅔, or ½, among others, of the transillumination step size. In some embodiments, at least one end of the photoluminescence range may be within about 10-30 micrometers of the candidate focal position.

The set of photoluminescence focal positions may be composed of a predetermined, fixed number of focal positions, or at least a predetermined, but potentially variable number of focal positions. If the predetermined number of focal positions is not sufficient to find the best photoluminescence focal position, one or more additional focal positions may be added to the set, to expand the range of the set, until the contrast peak can be identified. (For example, the focal positions for the predetermined number of focal positions all may be above or below best photoluminescence focal position.) The set may be expanded in the direction in which contrast increases.

A photoluminescence image(s) of the sample may be collected at the photoluminescence focal position(s) obtained, indicated at 160. One or more photoluminescence images may be collected at a single photoluminescence focal position, if the focal position was obtained directly from the candidate focal position. Alternatively, a fixed or variable set of photoluminescence images may be collected over a fixed or variable range of focal positions to produce a z-stack of photoluminescence images for refining the candidate focal position.

A value of a focus metric may be calculated for each image of the photoluminescence stack, as described above for transillumination images. However, in contrast to transillumination, the values of the focus metric for the stack of photoluminescence images may produce only a single peak. A focal position for the apex of the single peak may be determined by any suitable approach, such as fitting a curve to the data points, as described above for transillumination. The focal position at the apex of the single peak may be deemed the best focal position for photoluminescence.

Further photoluminescence images may or may not be collected from the same field of view of the sample. In some embodiments, one or more photoluminescence images from the z-stack may be selected as being sufficiently close to the best (theoretical) focal position at the apex of the contrast peak and/or as having sufficient quality, and no further imaging at the field of view may be conducted. In some embodiments, the best theoretical focal position may be compared to the closest focal position tested for the z-stack of photoluminescence images. If the best theoretical focal position is not within a threshold proximity to the closest focal position tested, the microscope system may be adjusted to the best photoluminescence focal position (the apex of the contrast peak), and at least one additional photoluminescence image may be collected.

Two or more images from a stack of transillumination images and/or two or more images from a stack of photoluminescence images may be at least partially combined with one another by image processing to produce one or more additional images. A digital phase image may be created by combining two or more of the transillumination images of a stack, optionally on a pixel-by-pixel basis. Images forming left contrast peak 130a may exhibit contrast inversion relative to corresponding images forming right contrast peak 130b (see FIG. 3). Accordingly, a digital phase image may be created by combining a plurality of transillumination images of the stack, including a pair of images that exhibit contrast inversion relative to one another and/or that are represent focal positions above and below the focal position at which a local contrast minimum occurs for the image stack (i.e., the nadir of contrast valley 132, see FIG. 3). The images may, for example, be combined by summing the intensity values of corresponding pixels for the plurality of transillumination images. Alternatively, or in addition, a composite photoluminescence image may be created from two or more photoluminescence images of a stack. The composite image may be a z-axis projection of the pixels with higher contrast from the two or more images. In other words, each region of the composite image may be composed selectively of pixels from whichever one of the images has the best contrast in that region.

The method steps described above are suitable for finding a candidate focal position and a best (or nominally best) photoluminescence focal position for the initial field of view of a sample holder and/or sample. These method steps can be modified significantly for subsequent fields of view with the same sample holder or sample, after at least one candidate focal position and/or best photoluminescence focal position has been obtained for the initial field of view. The subsequent fields of view represent different locations (e.g., wells) across the sample holder, which may or may not be fluidically isolated, spatially separated, and/or discrete from one another. In some embodiments, such as with a low power objective, the same candidate focal position and/or the same best (or nominally best) photoluminescence focal position obtained for the initial location (and initial field of view) may be used for all subsequent locations of the same sample holder, without modification. Alternatively, a candidate focal position and/or a best photoluminescence focal position may be determined separately for one or more subsequent locations. The transillumination range tested for each of the subsequent locations may have an endpoint that is adjusted with respect to the range for the initial location, based on the travel tilt of the stage. In other embodiments, the same candidate focal position may be used for all subsequent locations of the same sample holder, but the best photoluminescence focal position may be determined from a z-stack of photoluminescence images collected for each subsequent location. In still other embodiments, a candidate focal position and/or a best photoluminescence focal position may be obtained for only a subset of the locations of interest of a sample holder (e.g., every other well of a plate, the four wells closest to the corners of the plate, etc.), and other candidate focal positions or best photoluminescence focal positions may be determined by interpolation and/or extrapolation.

A travel tilt of the stage may be measured, to identify a suitable offset to be applied to a transillumination range, a candidate focal position, a photoluminescence range, and/or a best photoluminescence focal position for subsequent locations of the sample holder. To illustrate travel tilt with a specific example, a 96-well plate (8 rows×12 columns) may have a well-to-well spacing of 9 mm. The travel tilt may be determined to be 24 micrometers of z-axis offset per 72 mm (8 wells) of stage travel in a direction parallel to the columns (i.e., a z-offset of 3 micrometers/well along each column of wells), and 48 micrometers of z-axis offset per 108 mm of stage travel parallel to the rows (i.e., a z-offset of 4 micrometers/well along each row of wells). Accordingly, the indicated offsets may be applied to the transillumination range, the candidate focal position, the photoluminescence range, and/or the best (or nominally best) photoluminescence focal position for other wells of the plate based on the corresponding value(s) or range from an initial well tested. In this way, the wells of the plate can be imaged significantly faster.

Fiducials may be imaged to determine the travel tilt of the stage and/or to provide an estimate of the position of a sample along the z-axis (e.g., to facilitate choosing a range of focal positions for transillumination imaging and/or photoluminescence imaging). The fiducials may be provided by the sample holder or the stage. Exemplary fiducials are described in Example 5.

III. Examples

The following examples describe selected aspects and embodiments of the present disclosure related to a microscope imaging system with transillumination-based autofocusing, and methods of the using the microscope imaging system. These examples are included for illustration and are not intended to limit or define the entire scope of the present disclosure.

Example 1. Determination of a Candidate Focal Position

Figure 5:
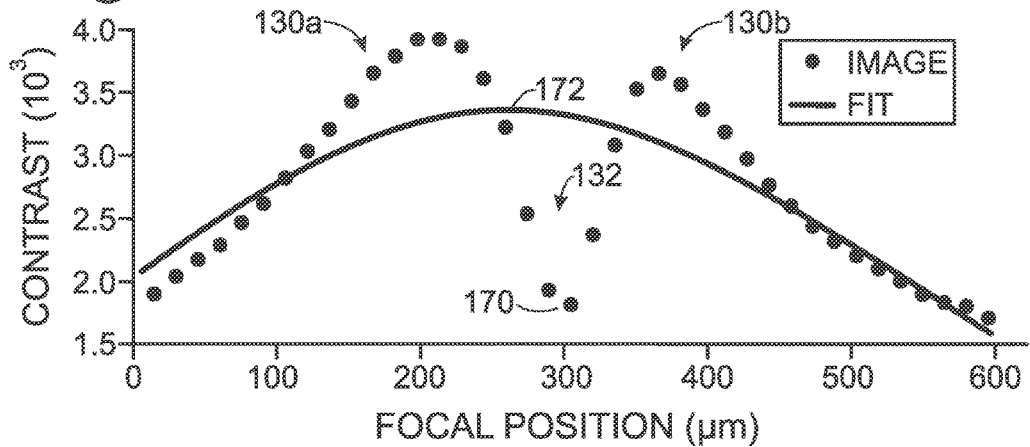
FIG. 5 is a graph showing data obtained with an embodiment of the microscope system of FIG. 1A, with the graph plotting (as points) a contrast measure (Vollath F4) as a function of focal position for a relatively dense stack of bright-field images obtained with a 4× objective located at focal position intervals (steps) of 15 micrometers, and with a one-term Gaussian curve fitted to the points.
Figure 6:
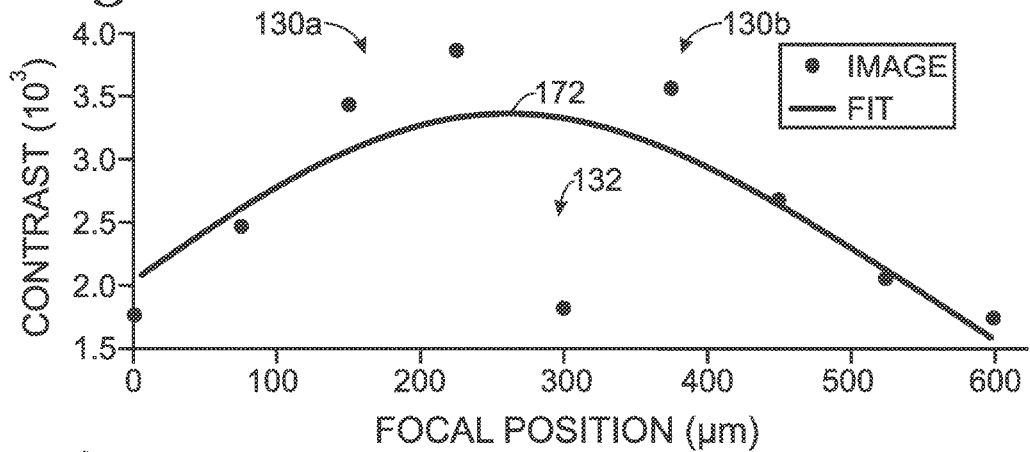
FIG. 6 is a graph showing data and a fitted curve obtained as in FIG. 5, but with a relatively sparse stack of images obtained at focal position intervals (steps) of 75 micrometers.

This example describes an exemplary determination of a candidate focal position for photoluminescence imaging based on the contrast values of a stack of bright-field images taken at two different stack densities; see FIGS. 5 and 6.

FIG. 5 shows a graph presenting data obtained with an embodiment of the microscope system of FIG. 1A operating in a transillumination configuration. The graph plots a measure of contrast (Vollath F4) (also called a focus metric) as a function of focal position for images collected from HeLa cells contained by wells of a 96-well plate. A relatively dense stack of bright-field images was obtained with a 4× objective located at focal position intervals of 15 micrometers. Each image provides a point on the graph. A one-term Gaussian curve having a single peak may be fitted to the points, even though the points form two contrast peaks. The range of focal positions tested is 600 micrometers to produce 40 images. The effective depth of field is approximately 100 micrometers. The best focus for photoluminescence, determined separately, is approximately 306 micrometers, which is close to a nadir 170 of a contrast valley 132 produced conceptually by connecting the data points with a curved line. Valley 132 is located between a pair of contrast peaks 130a, 130b as in FIG. 3. An apex 172 of a single broad peak of the Gaussian curve is located at about 270 micrometers, more than 30 micrometers from nadir 170 of valley 132.

FIG. 6 shows another graph presenting data and a fitted curve obtained as in FIG. 5, but with a relatively sparse stack of bright-field images collected at focal position intervals of 75 micrometers. Here, only nine images were collected, which is undersampling. Nevertheless, the candidate focal position identified is within 5 micrometers of that found in FIG. 5, after collection of only one-fifth as many images. The difference in candidate focal position between FIGS. 5 and 6 is less than 5% of the transillumination depth of field. The total error is approximately 40 micrometers from the best photoluminescence focal position, which is within the photoluminescence depth of field, allowing the candidate focal position to be chosen and used as a nominally best photoluminescence focal position.

Example 2. Determination of Candidate and Best Focal Positions

Figure 7:
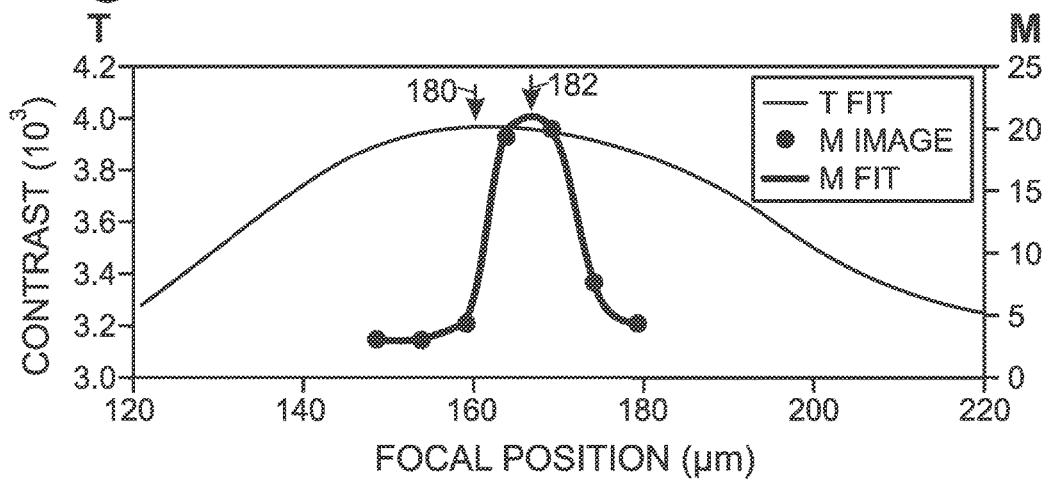
FIG. 7 is a graph plotting a contrast measure (Vollath F4) as a function of focal position, with data in the graph obtained with an embodiment of the microscope system of FIGS. 1A and 1B equipped with a 20× objective, and with the graph showing a fitted Gaussian curve ("T fit") for bright-field images, and individual points and a fitted curve for photoluminescence images ("M image" and "M fit," respectively).

This example describes exemplary determination of a candidate focal position and a best focal position for photoluminescence imaging, where focal positions for a stack of photoluminescence images are selected based on a candidate focal position determined from a stack of bright-field (transillumination) images; see FIG. 7.

FIG. 7 shows a graph plotting a measure of contrast (Vollath F4) as a function of focal position. The data in the graph was obtained with an embodiment of the microscope system of FIGS. 1A and 1B equipped with a 20× objective (0.45 NA) and operating in transillumination mode followed by epi-illumination mode. The graph shows a fitted, representative single-term Gaussian curve ("T fit") for the contrast of bright-field images collected from one of the cell lines (CHO, NIH3T3, PC-12, or U2OS) contained in wells of a 96-well plate. Also, individual data points and a fitted, representative Gaussian curve are shown on the graph for a stack of photoluminescence images collected from the same cell line and field of view. Arrows 180, 182 mark the respective apices of the contrast measure for the bright-field images and the photoluminescence images, and are only about 7 micrometers apart. The candidate focal position is identified by arrow 180, and the best photoluminescence focal position by arrow 182. The candidate focal position served as a guide for selection of a set of focal positions for the photoluminescence images. For this set of experiments performed on the various cells lines contained in the wells, 10-15 images were used to find each candidate focal position and up to 7 images to find each best photoluminescence focal position. The number of images needed to find the best photoluminescence focal position may, for example, be determined at least in part by characteristics of the sample, such as the sample thickness and the particular cell component(s) that has been stained.

Example 3. Best Focus Determination with a Predefined Number of Images

This example describes exemplary determination of a best focal position for photoluminescence imaging with a low power objective (4×) from a predefined number of photoluminescence images; see FIG. 8.

FIG. 8 shows a graph plotting an offset of the best focal position for photoluminescence as a function of the number of photoluminescence images collected. The offset is with respect to the candidate focal position determined with transillumination as in Examples 1 and 2. The data in the graph was obtained with an embodiment of the microscope system of FIGS. 1A and 1B equipped with a 4× objective and operating separately in transillumination and epi-illumination modes. The study was performed with eight different cell lines and with a preset minimum of five photoluminescence images for each photoluminescence image stack. No consistent offset of the best focal position was observed for the various cell lines. A stack of five photoluminescence images was sufficient in each case to determine the best focal position for photoluminescence.

The results show that the need to refocus is minimal within the expected depth of field. In other words, a candidate focal position obtained from transillumination images may be used directly for photoluminescence imaging, optionally with a mathematically applied offset. If refocusing is needed to refine the candidate focal position, this can be achieved in each case tested with only five transillumination images.

Example 4. Best Focus Determination with a Variable Number of Images

This example describes exemplary determination of a best focus for photoluminescence imaging with a medium power objective (20×) from a variable number of photoluminescence images; see FIG. 9.

FIG. 9 shows a graph plotting an offset of the best focal position for photoluminescence as a function of the number of photoluminescence images collected. The offset is with respect to a candidate focal position determined with transillumination as in Examples 1 and 2. The data in the graph was obtained with an embodiment of the microscope system of FIGS. 1A and 1B equipped with a 20× objective and operating separately in transillumination and epi-illumination modes. The study was performed with eight different cell lines and with a predefined minimum size of five photoluminescence images in each stack. Additional images were added successively to the photoluminescence stack until the photoluminescence contrast peak could be identified, if the position of the contrast peak was not identifiable with only five images. The best focal position for photoluminescence was found with seven or fewer images for all but one of the locations, over a span of 25 micrometers of offset.

Example 5. Fiducials for Tilt Compensation and/or Estimation of a Z-Axis Sample Position This example describes exemplary fiducials and uses thereof. The fiducials may facilitate compensation for stage tilt that offsets locations within a sample holder from one another along the optical axis when each location is placed on the optical axis. The fiducials also or alternatively may be imaged to estimate a sample position along the z-axis; see FIGS. 10-12.

Figure 10:
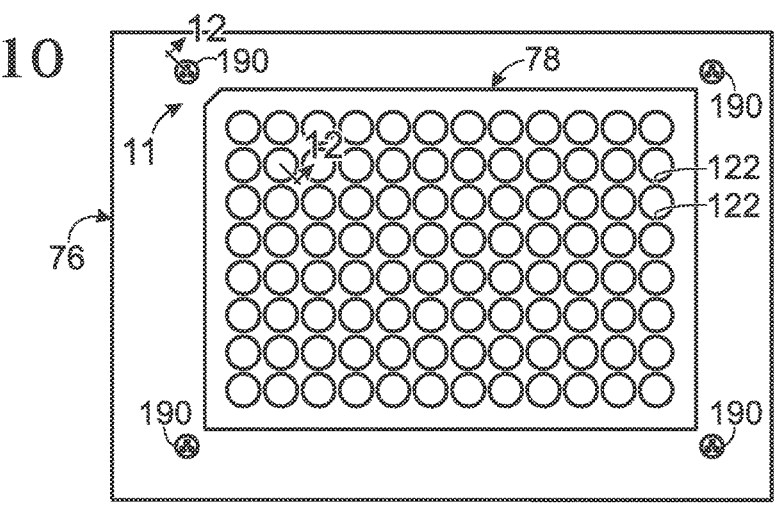
FIG. 10 is a plan view of a stage of the microscope system FIG. 1A, with the stage including a plurality of fiducials and supporting a sample holder.

FIG. 10 shows stage 76 of microscope system 50 of FIG. 1A. Stage 76 is supporting a sample holder 78 and includes a plurality of optically detectable fiducials 190. The fiducials may be formed integrally with the stage or may be removable, such as being held by a removable frame that rests on the body of the stage. The frame may be configured to receive and hold the sample holder. Three or more fiducials may be present. In the depicted embodiment, four fiducials 190 are disposed outside but near the periphery of the sample holder (e.g., near the four corners of the sample holder).

Figure 11:
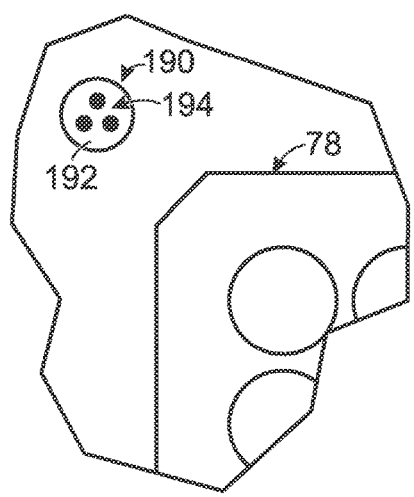
FIG. 11 is a fragmentary view of the stage and sample holder of FIG. 10, taken generally at the region indicated by "11" in FIG. 10 around one of the fiducials.

FIG. 11 shows a magnified view of one of fiducials 190. The fiducial may have a body 192, and a pattern 194 formed on a top side (or a bottom side) of the body. The pattern may, for example, be etched into the body or may be generated by depositing a layer of material onto the body. An exemplary material is chrome. The layer of material may alter transmission of light through the body, such as by absorbing, reflecting, refracting, or scattering incident light, among others. The pattern may cover only a portion of the top side (or bottom side) of body 192, such that elements of the pattern produce regions of high contrast at their peripheries. Accordingly, the pattern of each fiducial may be imaged over a range of focal positions with transillumination to identify a best focus for transmitted light. The fiducials may have known elevations relative to one another on the z-axis when the stage exhibits no tilt. For example, the fiducials may be at the same elevation with a stage that remains perfectly horizontal. Accordingly, the best transillumination focus determined for the fiducials can be compared to the known elevations of the fiducials in the absence of tilt, to determine the extent, if any, of stage travel tilt.

Figure 12:
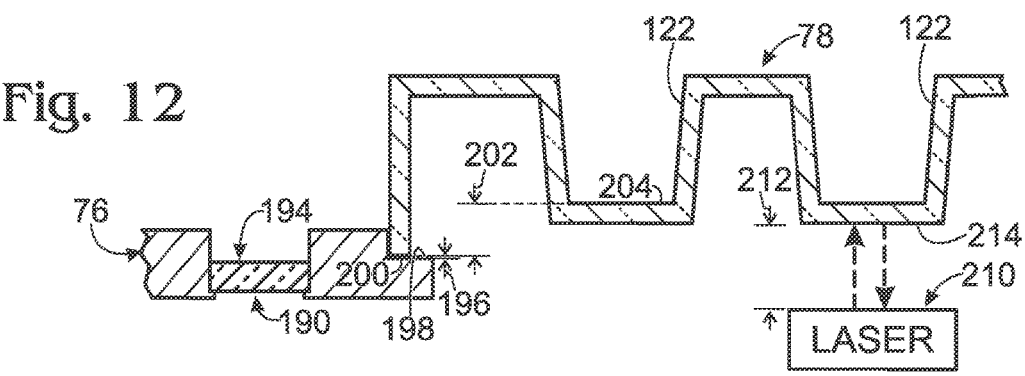
FIG. 12 is a somewhat schematic, sectional view of the stage and sample holder of FIG. 10, taken generally along line 12-12 of FIG. 10.

FIG. 12 shows a sectional view of stage 76 and sample holder 78 of FIG. 10. The best transillumination focus for fiducial 190 may be used to estimate a best transillumination focal position for a sample, based on known vertical offsets of the system. The elevation of pattern 194 on the fiducial corresponds to the best transillumination focus for fiducial 190. A vertical offset 196, if any, of a shelf 198 relative to pattern 194 may be known. In the depicted embodiment, there is substantially no vertical offset. The bottom edge 200 of sample holder 78, resting on shelf 198, has the same vertical offset. A value for a vertical offset 202 from bottom edge 200 to a floor 204 of a nearby well 122 may be available from the manufacturer of the sample holder. Accordingly, a rough estimate of the candidate focal position for one or more of the wells can be obtained by applying vertical offsets 196 and 202 to the best transillumination focal position obtained for one or more of the fiducials.

In other embodiments, the stage tilt may be determined with an optical measuring device 210, such as laser-based device, located below stage 76 of the microscope system. Device 210 may measure a vertical distance 212 between device 210 and a bottom side 214 of the sample holder at a plurality of locations of the sample holder. Changes to the vertical distance when different locations are placed on the optical axis indicate the stage travel tilt.

Example 6. Selected Embodiments

This example describes selected embodiments of the present disclosure as a series of indexed paragraphs.

1. A method of imaging a sample including biological cells, the method comprising: (A) detecting light transmitted through the sample for a first set of focal positions to collect a first stack of images; (B) calculating values of a focus metric for the first stack of images; (C) determining a candidate focal position based on the values; and (D) detecting photoluminescence from the sample for a second set of focal positions to collect a second stack of images, wherein the second set of focal positions defines a smaller range than the first set of focal positions, and wherein at least one focal position of the second set of focal positions is based on the candidate focal position.

2. The method of paragraph 1, wherein the second set of focal positions have a smaller step size than the first set of focal positions.

3. The method of paragraph 2, wherein the step size of the first set of focal positions is at least 50% larger than the step size of the second set of focal positions.

4. The method of any of paragraphs 1 to 3, further comprising a step of determining an exposure time for each image of the second stack of images based on photoluminescence detected only at an initial focal position of the second set of focal positions.

5. The method of any of paragraphs 1 to 4, further comprising a step of combining at least two images of the first stack to create a digital phase image of the sample, wherein a pair of the at least two images of the first stack represent focal positions that are respectively above and below the candidate focal position.

6. The method of any of paragraphs 1 to 5, further comprising a step of combining multiple images of the second stack of images to create a composite photoluminescence image including image regions, wherein each of the image regions is provided predominantly or exclusively by one of the multiple images having a best focus for the image region.

7. The method of any of paragraphs 1 to 6, wherein the candidate focal position is intermediate a pair of peaks for the focus metric, and wherein the step of determining a candidate focal position includes (i) a step of fitting a curve to data points defined by the values of a focus metric and the first set of focal positions for the first stack of images, and (ii) a step of obtaining the candidate focal position from the curve.

8. The method of paragraph 7, wherein the curve has a single peak within a range defined by the first set of focal positions, and wherein the step of determining a candidate focal position includes a step of finding a focal position for an apex of the single peak.

9. The method of any of paragraphs 1 to 8, wherein the candidate focal position is within about 20 micrometers of a best focal position for detecting photoluminescence from the sample.

10. The method of any of paragraphs 1 to 9, further comprising (i) a step of calculating values of a focus metric for the second stack of images, and (ii) a step of finding a best focal position for detecting photoluminescence from the sample based on the values for the second stack of images.

11. The method of paragraph 10, further comprising a step of adjusting focus according to the best focal position after the step of finding a best focal position, and a step of collecting a photoluminescence image of the sample after the focus is adjusted.

12. The method of paragraph 10 or 11, wherein the step of finding a best focal position includes a step of identifying a peak for photoluminescence contrast within the smaller range of focal positions.

13. The method of paragraph 12, wherein the step of finding a best focal position includes a step of selecting one of the focal positions of the second set of focal positions as the best focal position for being closest to an apex of the peak.

14. The method of paragraph 12, wherein the step of finding a best focal position includes a step of selecting a best focal position that is different from each focal position of the second set of focal positions.

15. The method of paragraph 14, wherein the step of detecting photoluminescence from the sample for a second set of focal positions includes a step of detecting photoluminescence from a predetermined number of focal positions to collect a set of photoluminescence images, and a step of determining whether a contrast peak is identifiable from the set of photoluminescence images.

16. The method of paragraph 15, further comprising a step of adding one or more focal positions to the predetermined number of focal positions to create one or more expanded sets of photoluminescence images, until a contrast peak is identifiable from an expanded set of photoluminescence images, if the contrast peak is not identifiable from the predetermined number of focal positions.

17. The method of any of paragraphs 1 to 16, wherein the steps of detecting light, calculating values, and determining a candidate focal position are performed for two or more locations created by a sample holder, and wherein the two or more locations are separated horizontally from one another.

18. The method of paragraph 17, wherein the sample holder is supported by a stage that is movable to place each of the two or more locations on an optical axis, further comprising a step of determining a tilt of the stage based on detection of light transmitted through the two or more locations.

19. The method of paragraph 18, further comprising a step of selecting a range of focal positions for at least one other location of the sample holder based on the tilt of the stage.

20. The method of any of paragraphs 1 to 19, wherein the sample is held by a sample holder supported by a stage, wherein the stage is movable to place different locations of the sample holder on an optical axis, and wherein the stage includes a plurality of fiducials, further comprising a step of imaging the fiducials to determine a travel tilt of the stage.

21. A method of imaging a sample including biological cells, the method comprising: (A) detecting light transmitted through the sample for a set of focal positions to collect a stack of images; (B) calculating values of a focus metric for the stack of images; (C) determining a candidate focal position based on the values; (D) obtaining a photoluminescence focal position based on the candidate focal position; and (E) detecting a photoluminescence image of the sample at the photoluminescence focal position.

22. The method of paragraph 21, wherein the step of obtaining a photoluminescence focal position includes (i) a step of assigning the candidate focal position as the photoluminescence focal position, or (ii) a step of calculating the photoluminescence focal position by applying a predetermined offset to the candidate focal position.

23. The method of paragraph 21, wherein the candidate focal position is intermediate a pair of peaks for the focus metric, and wherein the step of determining a candidate focal position includes (i) a step of fitting a curve to data points defined by the values of a focus metric and the set of focal positions for the stack of images, and (ii) a step of obtaining the candidate focal position from the curve.

24. The method of paragraph 23, wherein the curve has a single peak within a range defined by the set of focal positions, and wherein the step of determining a candidate focal position includes a step of finding a focal position for an apex of the single peak.

25. The method of any of paragraphs 21 to 24, wherein the set of focal positions is a first set of focal positions and the stack of images is a first stack of images, wherein the step of obtaining a photoluminescence focal position includes a step of detecting photoluminescence from the sample for a second set of focal positions to collect a second stack of images, and wherein at least one focal position of the second set of focal positions is based on the candidate focal position.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of imaging a sample including biological cells, the method comprising:
   detecting light transmitted through the sample for a first set of focal positions to collect a first stack of images, wherein the images of the first stack are bright-field images;
   calculating values of a focus metric for the first stack of images, wherein the values define only two peaks for the focus metric;
   determining a candidate focal position based on the values, wherein the candidate focal position is intermediate focal positions corresponding to the two peaks; and
   detecting photoluminescence from the sample for a second set of focal positions to collect a second stack of images, wherein the second set of focal positions defines a smaller range than the first set of focal positions, and wherein at least one focal position of the second set of focal positions is based on the candidate focal position.

2. The method of claim 1, wherein the second set of focal positions has a smaller step size than the first set of focal positions.

3. The method of claim 1, further comprising a step of determining an exposure time for each image of the second stack of images based on photoluminescence detected only at an initial focal position of the second set of focal positions.

4. The method of claim 1, further comprising a step of combining at least two images of the first stack to create a digital phase image of the sample, wherein a pair of the at least two images of the first stack represent focal positions that are respectively above and below the candidate focal position.

5. The method of claim 1, further comprising a step of combining multiple images of the second stack of images to create a composite photoluminescence image including image regions, wherein each of the image regions is provided predominantly or exclusively by one of the multiple images having a best focus for the image region.

6. The method of claim 1, wherein the step of determining a candidate focal position includes (i) a step of fitting a curve to data points defined by the values of a focus metric and the first set of focal positions for the first stack of images, and (ii) a step of obtaining the candidate focal position from the curve.

7. The method of claim 6, wherein the curve has a single peak within a range defined by the first set of focal positions, and wherein the step of determining a candidate focal position includes a step of finding a focal position for an apex of the single peak.

8. The method of claim 1, further comprising (i) a step of calculating values of a focus metric for the second stack of images, and (ii) a step of finding a best focal position for detecting photoluminescence from the sample based on the values for the second stack of images.

9. The method of claim 8, wherein the step of finding a best focal position includes a step of identifying a peak for photoluminescence contrast within the smaller range of focal positions.

10. The method of claim 9, wherein the step of finding a best focal position includes a step of selecting one of the focal positions of the second set of focal positions as the best focal position for being closest to an apex of the peak.

11. The method of claim 8, wherein the step of finding a best focal position includes a step of selecting a best focal position that is different from each focal position of the second set of focal positions.

12. The method of claim 1, wherein the step of detecting photoluminescence from the sample for a second set of focal positions includes a step of detecting photoluminescence from a predetermined number of focal positions to collect a set of photoluminescence images, and a step of determining whether a contrast peak is identifiable from the set of photoluminescence images.

13. The method of claim 12, further comprising a step of adding one or more focal positions to the predetermined number of focal positions to create one or more expanded sets of photoluminescence images, until a contrast peak is identifiable from an expanded set of photoluminescence images, if the contrast peak is not identifiable from the predetermined number of focal positions.

14. The method of claim 1, wherein the sample is held by a sample holder supported by a stage, wherein the stage is movable to place different locations of the sample holder on an optical axis, and wherein the stage includes a plurality of fiducials, further comprising a step of imaging the fiducials to determine a travel tilt of the stage.

15. The method of claim 1, wherein the biological cells are stained only with one or more fluorescent dyes, if stained at all.

16. A method of imaging a sample including biological cells, the method comprising:

detecting light transmitted through the sample for a set of focal positions to collect a stack of bright-field images;

calculating values of a focus metric for the stack of bright-field images, wherein the values define only two peaks for the focus metric;

determining a candidate focal position based on the values, wherein the candidate focal position is intermediate focal positions corresponding to the two peaks;

obtaining a photoluminescence focal position based on the candidate focal position; and detecting a photoluminescence image of the sample at the photoluminescence focal position.

17. The method of claim 16, wherein the step of obtaining a photoluminescence focal position includes (i) a step of assigning the candidate focal position as the photoluminescence focal position, or (ii) a step of calculating the photoluminescence focal position by applying a predetermined offset to the candidate focal position.

18. The method of claim 16, wherein the step of determining a candidate focal position includes (i) a step of fitting a curve to data points defined by the values of a focus metric and the set of focal positions for the stack of bright-field images, and (ii) a step of obtaining the candidate focal position from the curve.

19. The method of claim 18, wherein the curve has a single peak within a range defined by the set of focal positions, and wherein the step of determining a candidate focal position includes a step of finding a focal position for an apex of the single peak.

20. The method of claim 16, wherein the biological cells are stained only with one or more fluorescent dyes, if stained at all.

* * * * *